US008003673B2

(12) United States Patent
Alder et al.

(10) Patent No.: US 8,003,673 B2
(45) Date of Patent: Aug. 23, 2011

(54) DAPTOMYCIN FOR THE TREATMENT OF BIOFILM AND CATHETER SALVAGE

(75) Inventors: Jeffrey Alder, Harvard, MA (US); Jared Silverman, Brookline, MA (US); Lawrence Mortin, Framingham, MA (US); Andrew Van Praagh, Chelmsford, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 827 days.

(21) Appl. No.: 11/916,089

(22) PCT Filed: May 31, 2006

(86) PCT No.: PCT/US2006/021006
§ 371 (c)(1),
(2), (4) Date: Nov. 30, 2007

(87) PCT Pub. No.: WO2006/130629
PCT Pub. Date: Dec. 7, 2006

(65) Prior Publication Data
US 2009/0298750 A1    Dec. 3, 2009

(51) Int. Cl.
*A01N 43/64* (2006.01)
*A61K 31/41* (2006.01)
*C07D 209/04* (2006.01)
*C07D 239/47* (2006.01)

(52) U.S. Cl. .......................... 514/359; 548/469; 514/272
(58) Field of Classification Search ................... 514/359; 548/469
See application file for complete search history.

(56) References Cited

U.S. PATENT DOCUMENTS
6,777,420 B2 *   8/2004   Zhi et al. ....................... 514/272

OTHER PUBLICATIONS

Cubicin® (daptomycin for injection) Label 1004—Sep. 2003.
Cubicin® (daptomycin for injection) Label 1004-1—Revised Aug. 2004.
Cubicin® (daptomycin for injection) Label 1004-2—Revised Jun. 2005.

* cited by examiner

*Primary Examiner* — Paul V. Ward
(74) *Attorney, Agent, or Firm* — Cubist Pharmaceuticals, Inc.

(57) ABSTRACT

Daptomycin can be used for biofilm treatment (particularly central venous catheter salvage for *S. epidermidis* infected catheters). Catheter salvage with daptomycin shows rapid cidality, activity against stationary phase bacteria, and penetration and activity in biofilms. The present inventions provide formulations, methods, and articles of manufacture useful for biofilm treatment or catheter salvage involving daptomycin. Particular formulations include daptomycin in lactated Ringer's solution having a rapid kill curve against the bacteria of the biofilm.

20 Claims, 12 Drawing Sheets

Figure 1. Stability of catheter infection, short term effects of daptomycin treatment, and correlation of CVC blood draw and harvested CVC (CFU/ml) counts.

Figure 2. Correlation between CFU determined by blood draw and from harvested catheters.

Figure 3. Efficacy of daptomycin and vancomycin against CVC infection [30 or 60 minute doses, days 6-9].

Figure 4. Efficacy of daptomycin and vancomycin therapy on metastatic infection.

Figure 5. Efficacy of daptomycin (Saline or Ringers formulations) and vancomycin in preventing re-emergence of CVC infection.

Figure 6. Efficacy of lock therapy (18 hour exposure QD x 3) on CVC infection.

Figure 7. Efficacy of lock therapy on metastatic infection.

Figure 8. Observation of CVC infection at the catheter tip and surrounding tissue of the vena cava.

Figure 8. Illustrating the blood-filled catheter's lumen and the hemorrhagic thrombus present at the interface between the catheter's outer surface and the vena cava's endothelium. After H&E staining, the catheter remained unstained and transparent. The blue double-head arrows show the thickness of the catheter (inner to outer surfaces). Bacterial colonies (bc, blue arrow) were observed attached to the inner surface of the catheter. Left image taken at 100x, and right image at 600x magnification.

Figure 9. Biofilm appearance at day 8 post infection.

Figure 9. After H&E staining, the catheter remained unstained and transparent. The left image identifies the biofilm containing the bacterial colonies (bc, blue arrows) attached to the inner surface of the catheter. Center images (Gram-stained) show the variable thickness of the biofilm material attached to the catheter's inner luminal surface. The image on the right illustrates the endothelial proliferation (thickening and cellular pilling), and the prominent subendothelial fibrous tissue. All images were taken at 600x magnification.

Figure 10. Biofilm appearance at day 12 post infection.

Figure 10. The left image, taken at 100x magnification, shows the catheter (traced) with a central protein cast filling the lumen (Gram stain). The central image identifies the biofilm containing the bacterial colonies (bc, blue arrows). The image on the right (Gram stain) illustrates the fibrillar appearance of the biofilm. Center and right images were taken at 600x magnification.

Figure 11. Histopathological evidence of daptomycin and vancomycin efficacy after 4 days of catheter instillation therapy.

Figure 11. From left to right, the images illustrate the CVC tissues from rats A1, A6, A12, and A17, respectively. The upper images are all H&E-stained and the bottom images are all Gram-stained. Biofilms containing true bacterial colonies (red and blue arrows) were identified only in the saline-treated rat (A1) and the vancomycin-treated rat (A17). Rat #A12, which received high-dose daptomycin, showed foci with pin-point-sized blue-staining round structures (Gram stain). These round structures surrounded or encircled cell membranes. These round objects were not interpreted to be bacterial colonies.

Figure 12. Activity of daptomycin and vancomycin at 5 mg/ml in saline against stationary phase *S. epidermidis*.

Figure 12. In saline, neither daptomycin nor vancomycin achieved cidal effect on the bacterial culture in stationary phase. The control culture showed a > 1 $\log_{10}$ decrease in counts over the 28 hours of the experiment.

Figure 13. Activity of daptomycin and vancomycin at 5 mg/ml in lactated Ringers against stationary phase *S. epidermidis*.

Figure 13. Daptomycin was rapidly cidal against stationary phase *S. aureus* in lactated Ringers solution. Vancomycin had no effect in this media. The control culture with no antibiotic showed a 1 $\log_{10}$ decrease in CFU over the 28 hours of the experiment.

ized jugular veins. *Omitted by error.*

DAPTOMYCIN FOR THE TREATMENT OF BIOFILM AND CATHETER SALVAGE

BACKGROUND OF THE INVENTION

Central venous catheters (CVCs) are used to provide medication to patients to treat conditions that might require longer courses of treatment, for example, pain, infection, or cancer, or to supply nutrition. A central venous catheter can be left in place longer than an intravenous catheter (IV), which delivers medications into a vein near the skin surface. Biofilms can occur in CVCs and they comprise an accumulation of bacteria, e.g. S. epidermidis, on and into the surface of the CVC. The biofilm can be difficult to treat because some bacteria may be in a stationary phase and/or the biofilm may be difficult to penetrate.

SUMMARY OF THE INVENTION

Biofilm treatment (and particularly central venous catheter salvage for S. epidermidis infected catheters) can be made with daptomycin. Catheter salvage with daptomycin might include rapid cidality, activity against stationary phase bacteria, and penetration and activity in biofilms. The present invention provides formulations, methods, and articles of manufacture useful for biofilm treatment or catheter salvage involving daptomycin. Particular formulations include daptomycin in lactated Ringer's solution.

DETAILED DESCRIPTION OF THE INVENTION

Overview of the In Vivo Model

A rat model of CVC infection was established using a glycocalyx-producing clinical isolates of S. epidermidis. Infection was monitored by blood draws through the infected catheter, and by determining bacterial burden in distal tissues at necropsy. Daptomycin in a simulation of therapy (30 minute infusion at 5 mg/ml) temporarily reduced catheter infections to a non-detectable level, but infection resurgence was common. Daptomycin in a simulation of lock therapy (18 hour lock at 5 mg/ml) was curative and prevented resurgence. Vancomycin in this model (curative in lock therapy) also had high levels of efficacy which is counter to perceived clinical experiences, although clinical data is very limited.

SPECIFIC EXAMPLES OF THE INVENTION

A. A Rat Model of CVC Infection

Male Sprague Dawley rats (~250 g) with catheterized jugular veins were used in these studies. Rat catheters (polyurethane tubing, 0.025 inch internal diameter) were inoculated with a culture of S. epidermidis at $5 \times 10^8$ CFU/ml. The total volume of the catheters is approximately 40 µl. The catheters were flushed with heparinized saline 1 hour after inoculation, and were maintained by daily flushes. The catheter infection was monitored by daily blood draws that were plated and quantified.

Daptomycin, vancomycin and nafcillin were used as therapy. Two different dosing regimes were used. The first mimicked clinical infusion with daptomycin administered at 5 mg/ml in the line for 30 minutes once daily compared to vancomycin at 5 mg/ml for 60 minutes twice daily, for a total of 4 days. The second regime simulated antibiotic lock therapy with an 18 hour exposure of daptomycin or vancomycin at 5 mg/ml, followed by a heparinized saline flush, daily for 3 days. In both regimes, the animals received parenteral doses of the appropriate antibiotic by subcutaneous route to simulate total body exposure (as it was not possible to administer the correct dosages through the line at 5 mg/ml). Most trials involved a therapy period, followed by a period of no antibiotic therapy to monitor for resurgence of infection due to surviving bacterial colonies.

Infection levels were monitored by daily blood draws through the infected catheter. For the terminal harvest, a final blood draw was taken and then the flushed catheter was harvested, and analyzed for surviving bacteria by sonication, vortexing, and plating. The vena cava, heart, lung, kidney, and spleen were assayed as potential metastatic infection sites by aseptic harvest, homogenization, and plating.

CVC Salvage Results in the Rat Model

Several different isolates of S. epidermidis were tested in the CVC model. Isolates 1315 and 1318 were chosen for further study based on infection of catheters and antibiotic susceptibility.

TABLE 1

Susceptibility of S. epidermidis isolates used in CVC studies.

| | Strain | MICs in ug/mL | | | | |
|---|---|---|---|---|---|---|
| | | Daptomycin | Linezolid | Nafcillin | Vancomycin | Rifampicin |
| 1315 | Staphylococcus epidermidis | 0.5 | 0.5 | 2 | 1 | <0.004 |
| 1316 | Staphylococcus epidermidis | 0.5 | 1 | 16 | 1 | 0.008 |
| 1317 | Staphylococcus epidermidis | 1 | 0.5 | 0.125 | 1 | >4 |
| 1318 | Staphylococcus epidermidis | 1 | 1 | >16 | 2 | end pts at 4, 0.03 & 0.008 |
| 1319 | Staphylococcus epidermidis | 1 | 0.5 | 16 | 1 | <0.004 |
| 1320 | Staphylococcus epidermidis | 0.5 | 1 | >16 | 1 | 0.008 |
| 119 | Staphylococcus epidermidis | 0.25 | 1 | 0.031 | 1 | 0.008 |
| 42 | Staphylococcus aureus | 0.5 | 2 | 0.125 | 0.25 | <0.004 |
| NCCLS Acceptable Limits for S. aureus #42 | | 0.25-1 | 1-4 | 0.12-0.5 | 0.5-2 | 0.004-0.016 |

TABLE 2

Based on establishment of productive infection and susceptibility, isolates 1315, 1318 and 1320 were used in the majority of the trials.

| Cubist Strain# | ATCC# | Description |
|---|---|---|
| 1315 | 35984 | In vitro biofilm model strain with reported oxacillin resistance; biosafety level one; AAC October 2003 pp 3145-3148; lyophilized culture stored in small 4C fridge in box. Purified genomic DNA available through the ATCC. Produces a polysaccharide adhesi |
| 1316 | 35983 | Slime producing strain, biosafety level two. Lyophilized culture stored in small 4C fridge in box. References available on ATCC website, and in micro strain binder. |
| 1317 | 49134 | Quality control strain, biosafety level two. No references available. |
| 1318 | 49461 | Quality control testing of MicroScan panels, biosafety level two. No references available. |
| 1319 | 700562 | Biosafety level two. Reported resistance to oxacillin, cefazolin, clindamycin, erythromycin and trimethoprim-sulfamethoxazole. No references available. |
| 1320 | 700565 | Biosafety level two. Reported resistance to ampicillin, oxacillin, penicillin, amoxicillin-clavulanate, piperacillin-tazobactam, cefazolin, cefotaxime, imipenem, ciprofloxacin, ofloxacin, clindamycin and erythromycin. No references available. |

Figure 1:
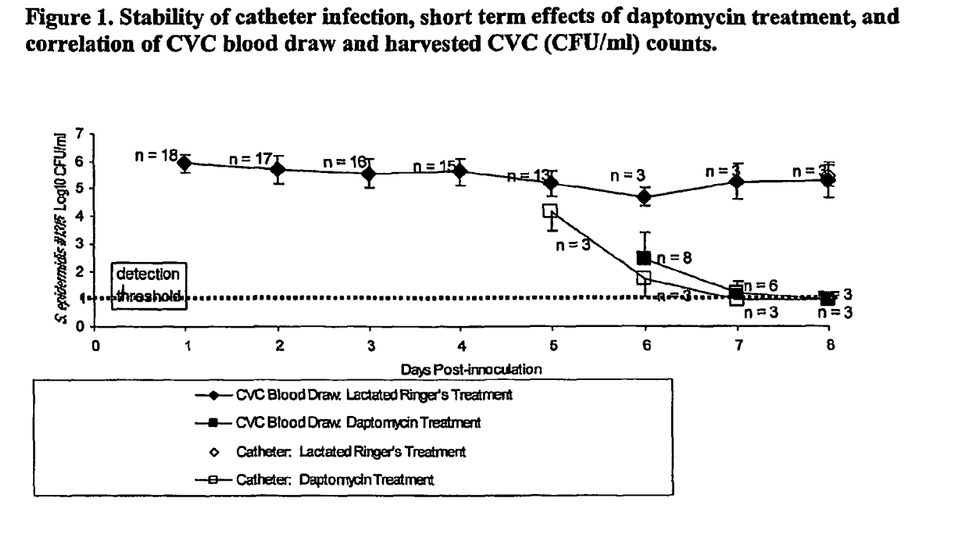
FIG. 1 shows the stability of catheter infection and short term effects of daptomycin treatment and correlation of CVC blood draw and harvested CVC (CFU/ml) counts.

FIG. 1 demonstrates that a stable CVC infection, as monitored by blood draw through the infected catheter, was maintained at 5 to 6 $\log_{10}$ CFU/ml from day 1 through day 8 post inoculation. CVC blood draw counts [solid symbols] were similar to the counts recovered from the harvested catheters [open symbols]. The pronounced effect of 30 minute daptomycin (in lactated Ringer's) doses given after blood draws on days 5-7 were noted by both blood draw and harvested catheter CFU counts [days 6-8].

Figure 2:
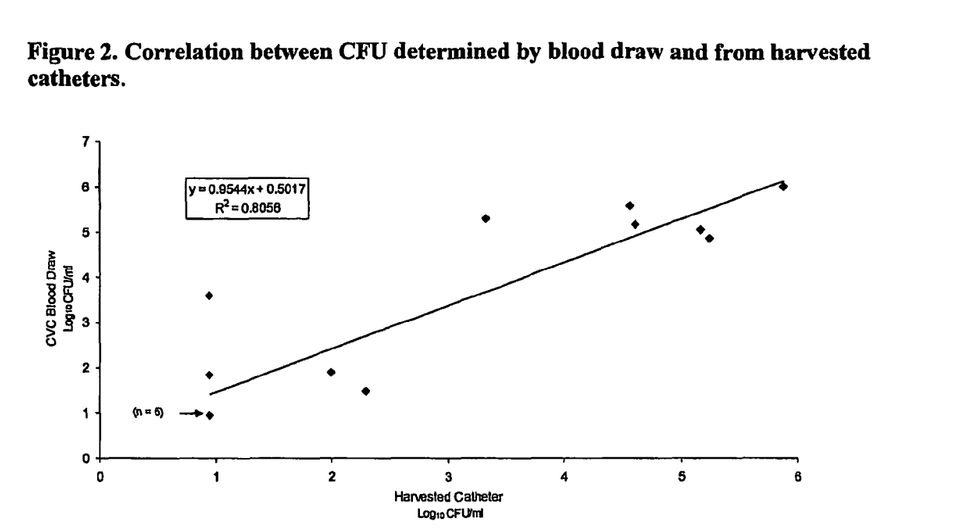
FIG. 2 demonstrates a correlation between CFU determined by blood draw and from harvested catheters.

FIG. 2 shows that there was a good correlation in CFU recovered by blood draws and by sonication of the harvested catheters ($R^2$=0.81).

Figure 3:
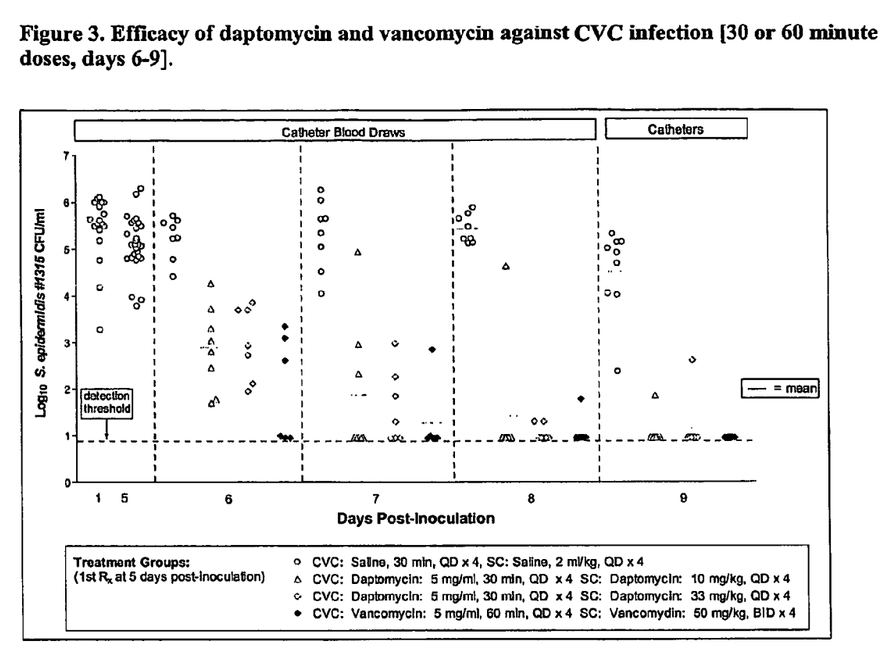
FIG. 3 compares the efficacy of daptomycin and vancomycin against CVC infection [30 or 60 minute infusion, days 6-9].

FIG. 3 illustrates the efficacy of daptomycin infusion therapy against CVC infection. Daptomycin (open triangles, open diamonds), dosed once a day, and vancomycin (closed diamonds), dosed twice a day, both reduced most catheter infections to a non-detectable level after three days of therapy (day 8). Harvested catheters (day 9) showed CFU counts similar to the blood draws. The saline treated CVC infection produced >1×10$^5$ CFU/ml blood throughout the course of the infection.

Figure 4:
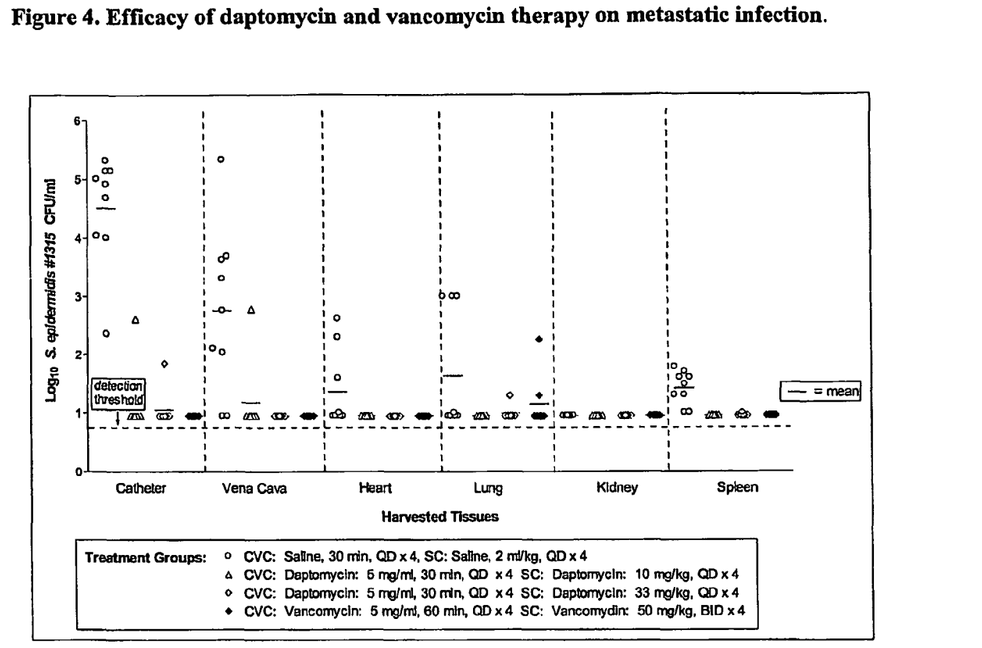
FIG. 4 compares the efficacy of daptomycin and vancomycin infusion therapy on metastatic infection.

FIG. 4 shows the efficacy of daptomycin and vancomycin infusion therapy on metastatic infection. Saline treated CVC infections showed metastatic infections in proportion to the proximity to the catheter tip. The vena cava, and to a lesser extent the lung and heart tissue all showed recoverable CFUs of S. epidermidis. The spleen and kidney showed little or no CFUs. Daptomycin and vancomycin therapies (same symbol key as FIG. 3) both showed very little metastatic infection at any site.

Figure 5:
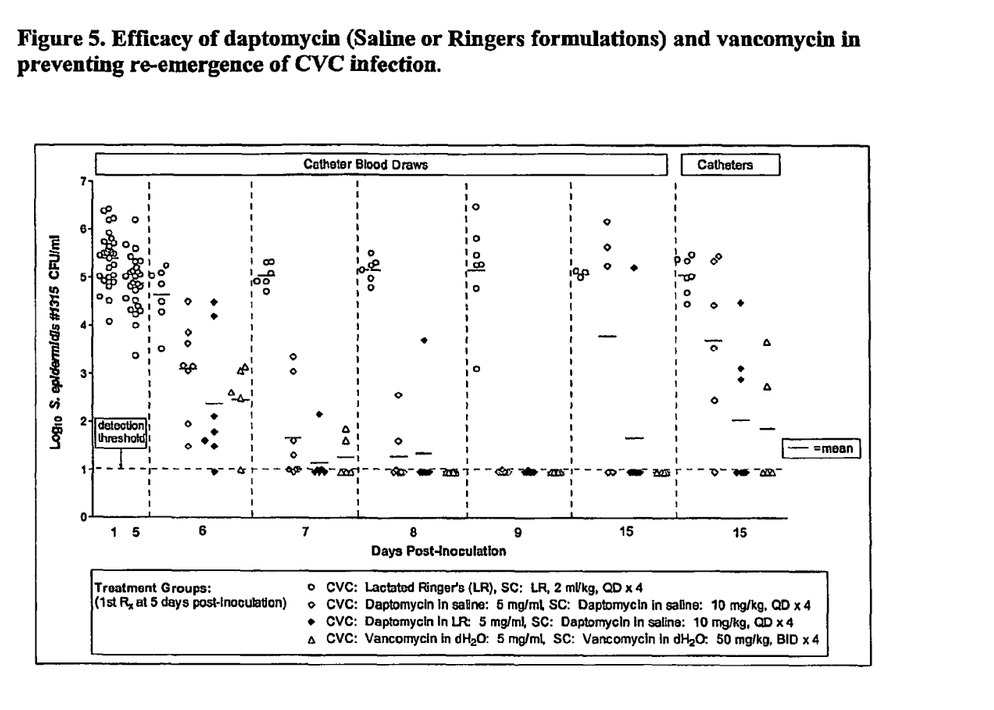
FIG. 5 compares the efficacy of daptomycin (saline and Ringer's infusion) and vancomycin in preventing re-emergence of CVC infection.

FIG. 5 records the efficacy of daptomycin (saline and lactated Ringer's infusion) and vancomycin in preventing reemergence of CVC infection. Daptomycin (30 minute doses, once a day, days 5-8) in saline [open diamonds] or Ringer's [closed diamonds] reduced infections to a non-detectable level by day 9. Vancomycin (60 min doses, twice a day, days 5-8) in dH2O (open triangles) produced negative blood draw cultures by day 8. After 6 days of antibiotic-free heparin flushes (day 15), 3/6 of the daptomycin-saline treated animals produced positive blood draws through the catheter. For the daptomycin-lactated Ringer's group, only 1/6 produced positive blood draws. The harvested catheter produced positive S. epidermidis CFUs in 5/6 of the daptomycin-saline group and 3/6 of the daptomycin-Ringer's group. The vancomycin treated animals produced 0/6 positive blood draws and 2/6 positive catheters on day 15. Daptomycin in lactated Ringer's was superior to daptomycin in saline for speed of response and to maintain efficacy.

Figure 6:
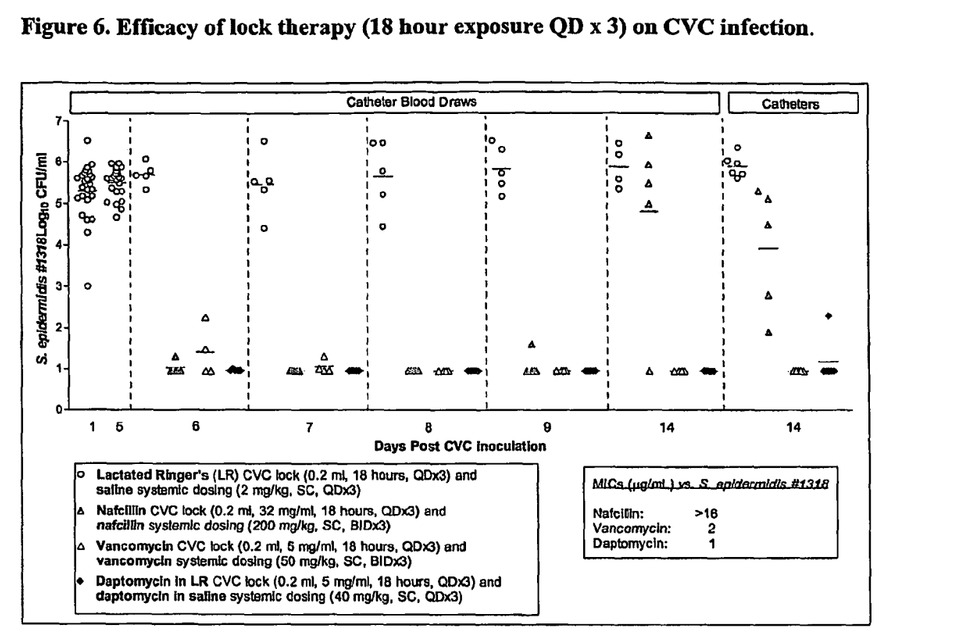
FIG. 6 compares the efficacy of lock therapy (18 hour exposure QD×3) on CVC infection.

FIG. 6 shows the efficacy of lock therapy (18 hour exposure QD×3) on CVC infection. All three antibiotics given by lock therapy (days 5, 6 and 7) resulted in temporarily cleared blood draws (day 8). Following 7 days of antibiotic-free heparin flushes, all of the nafcillin-treated animals produced positive catheters. For the daptomycin treated animal, 0/6 showed positive blood draws and 1/6 showed a positive catheter (low infection level) at harvest. None of the vancomycin treated animals showed positive blood draws or catheters.

Figure 7:
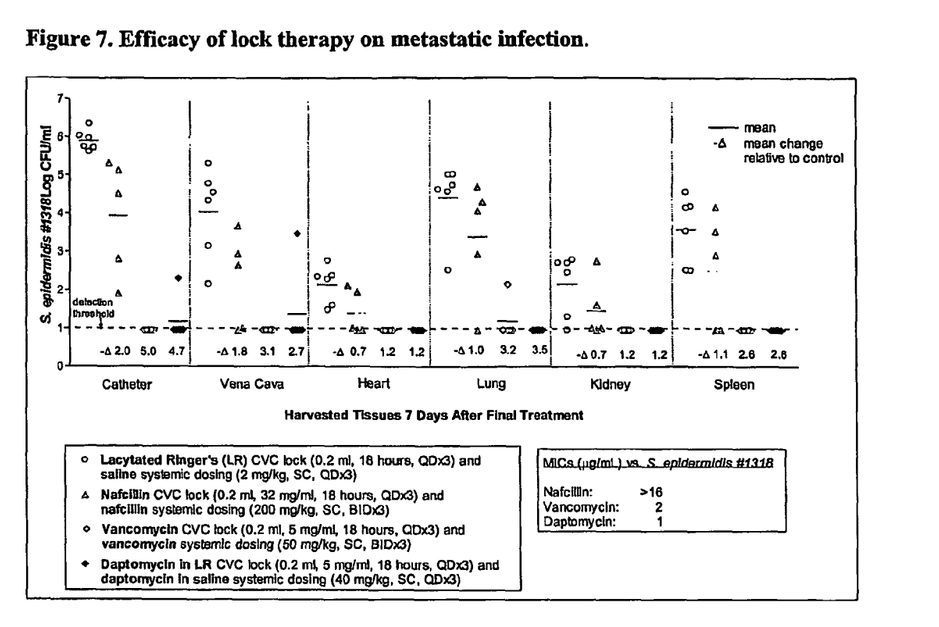
FIG. 7 shows the efficacy of lock therapy on metastatic infection.

FIG. 7 indicates the efficacy of lock therapy on metastatic infection. Both vancomycin and daptomycin lock therapy, combined with SC dosing, cleared and prevented reemergence of metastatic infection. A significant proportion of nafcillin-treated animals showed positive metastatic infections at multiple sites.

The nature of the CVC infection and resulting biofilms in the catheter was determined through histopathology. The data on histopathology can be summarized as follows:

1. Eight days after implantation, the rat central venous catheter model develops focal biofilms with or without bacterial colonies in the catheter's inner luminal surfaces. At this time point, the thickness of the biofilm varies between 7 to 15 microns.

2. After 12 days of implantation, the fibrils making up the inner luminal surface biofilm appear to be denser and more organized, and the biofilm layer is slightly thicker (up to 25 microns).

3. In the saline negative controls, bacterial colonies were present in the biofilm, and identified as Gram positive cocci.

4. Daptomycin treatment at 5 mg/mL via the catheter did not prevent biofilm formation, but prevented the growth and presence of Gram positive bacterial colonies in the biofilm. However, cocci-like, Gram positive individual round structures were noted.

5. Vancomycin treatment at 5 mg/mL via the catheter did not prevent biofilm formation, or completely the growth and presence of Gram positive bacterial colonies in the biofilm.

Figure 8:
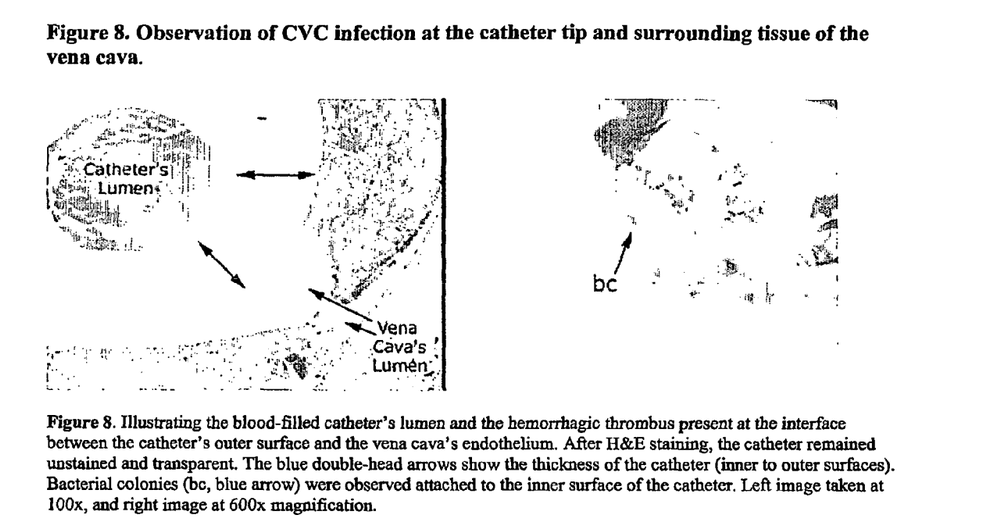
FIG. 8 depicts an observation of CVC infection at the catheter tip and surrounding tissue of vena cava.

FIG. 8 shows pictures of the CVC infection at the catheter tip and surrounding tissue of vena cava.

Figure 9:
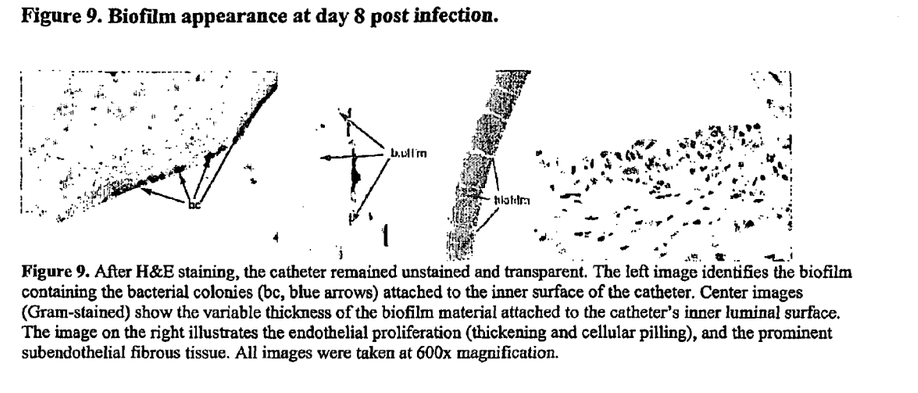
FIG. 9 shows the biofilm appearance at day 8 post infection.

At day 8 post infection, biofilms were present in most of the inner luminal surfaces of the indwelling catheter. The biofilms were tightly adhered to the surface. Biofilms were composed of eosinophilic fibrillar to granular material, admixed with variable numbers of basophilic granular bacterial colonies. Grams stains confirmed the bacterial colonies to be Gram positive cocci. Also, the Gram stained sections colored the biofilms as yellowish to golden fibrillar tissue and varied from <5 to 25 microns. Lastly, the endothelial surfaces showed mild hyperplasia, and sub-endothelial fibrous thickening. See FIG. 9 showing the biofilm appearance at day 8 post infection.

Figure 10:
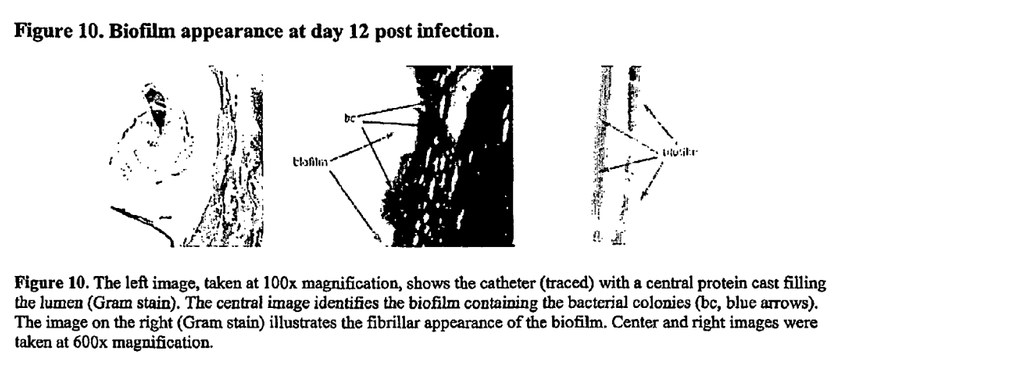
FIG. 10 shows the biofilm appearance at day 12 post infection.
Figure 11:
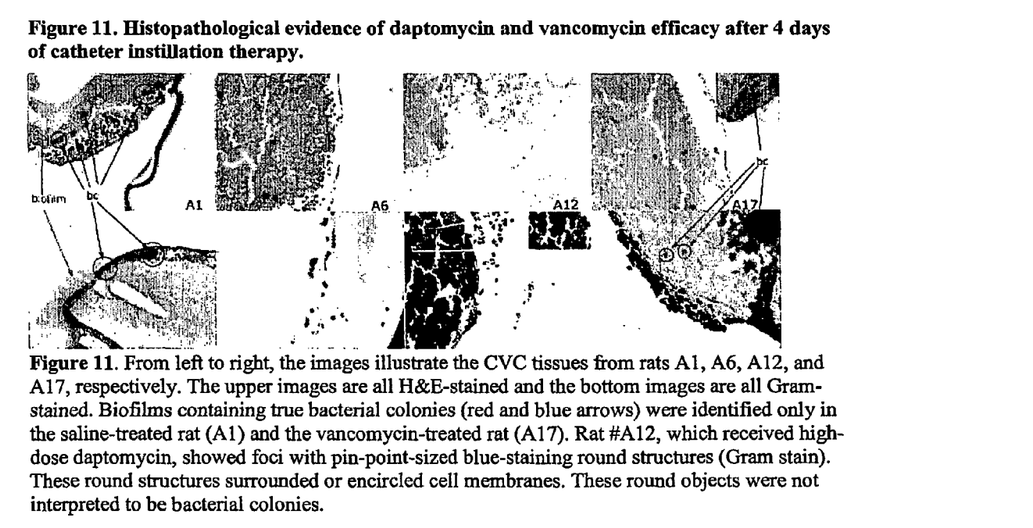
FIG. 11 compares the histopathological evidence of daptomycin and vancomycin efficacy after 4 days of infusion therapy.

At day 12 post infection in untreated rats, as in the previous time point, biofilms tended to be present in the inner luminal surfaces of the indwelling catheter, 5-25 microns thick, and contained variable numbers of basophilic granular bacterial colonies (confirmed by Gram stain). However, in contrast to the previous time point, focal portions of the luminal protein cast appeared to be more organized and contained numerous bluish bacterial colonies. See FIG. 10 showing the biofilm appearance at day 12 post infection. As shown in FIG. 10, the histopathological evidence of daptomycin and vancomycin efficacy by 30 and 60 minute instillation, respectively, against bacterial biofilms in vivo was investigated. Rat A1 served as negative control and received saline (2 mL/kg SC+saline via catheter); Rat A6 received low-dose daptomycin (10 mg/kg SC+5 mg/mL via catheter); Rat A12 received high-dose daptomycin (33 mg/kg SC+5 mg/mL via catheter); and Rat A17 received vancomycin (50 mg/kg SC+5 mg/mL via catheter). Tissues from the four rats were evaluated. FIG. 11, below, is a composite of the findings for all four rats.

FIG. 11 provides histopathological evidence of daptomycin and vancomycin efficacy after 4 days of infusion therapy. In FIG. 11, from left to right, the images illustrate the CVC tissues from rats A1, A6, A12, and A17, respectively. The upper images are all H&E-stained and the bottom images are all Gram-stained. Biofilms containing true bacterial colonies (red and blue arrows) were identified only in the saline-treated rat (A1) and the Vancomycin-treated rat (A17). Rat #A12, which received High-dose Daptomycin, showed foci with pin-point-sized blue-staining round structures (Gram stain). These round structures surrounded or encircled cell membranes. These round objects were not interpreted to be bacterial colonies.

Example 2

In vitro Model of Stationary Phase Bacteria

The impact of cidal activity of antibacterial compounds on stationary phase bacteria was assayed. Cultures of $S.$ $epidermidis$ and $S.$ $aureus$ were grown to stationary phase ($>1\times10^9$ and centrifuged, washed 2x, and then resuspended into saline or lactated Ringer's solution. The cultures were treated with either daptomycin or vancomycin at 5 mg/ml and the decrease in viable bacteria were measured through 24 hours to determine the kill kinetics.

Figure 12:
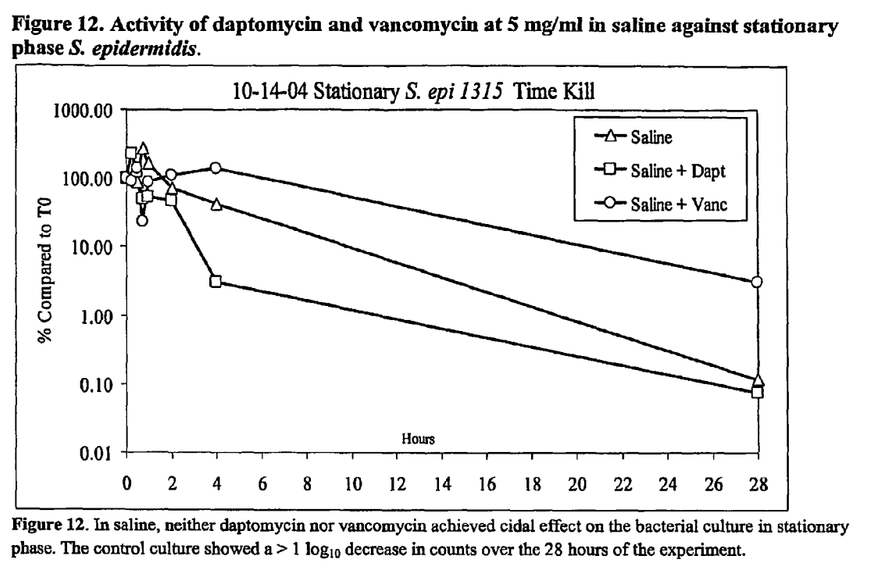
FIG. 12 compares the activity of daptomycin and vancomycin at 5 mg/ml in saline against stationary phase S. epidermidis.

In saline, neither daptomycin nor vancomycin had cidal activity against a stationary phase culture of $S.$ $epidermidis$. See FIG. 12.

Figure 13:
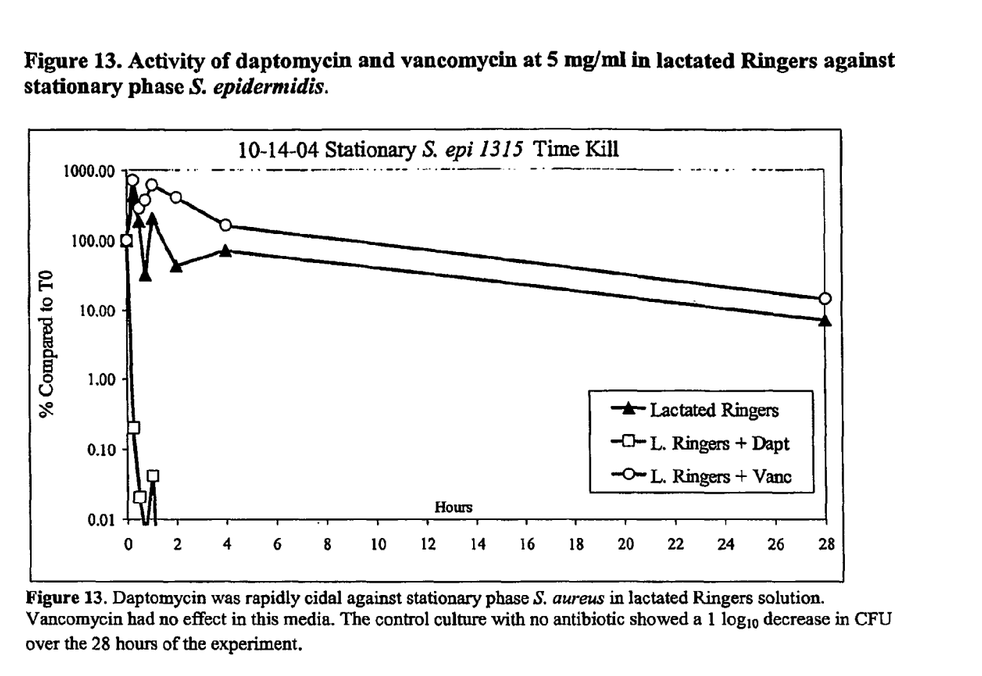
FIG. 13 shows the relative activity of daptomycin and vancomycin at 5 mg/ml in Lactated Ringer's against stationary phase S. epidermidis.

FIG. 13 compares the activity of daptomycin and vancomycin at 5 mg/ml in lactated Ringer's against stationary phase $S.$ $epidermidis$. In lactated Ringer's, daptomycin was rapidly cidal against a stationary phase culture of $S.$ $epidermidis$. One possible explanation for this is that lactated Ringer's solution provides a physiological concentration of calcium. Vancomycin had no cidal activity in lactated Ringer's.

Example 3

In vitro Model of Biofilm (R. Patel et al, 2005)

Methicillin-resistant coagulate negative staphylococci biofilms were grown to approximately $10^5$ cells per cm² for 24 h in glass test tubes, planktonic bacteria rinsed away and Mueller Hinton broth (calcium supplemented to 50 mg/mL in daptomycin tests) containing antimicrobials added to the tubes. The concentrations of antimicrobials studied were twofold dilutions from 64 to 1 μg/mL of daptomycin, rifampin, or daptomycin plus 0.5 μg/mL rifampin. The tests were incubated overnight in room air at 37° C. The cell density in rinsed biofilms was determined prior to addition of antimicrobials and after incubation. The change in bacterial density after incubation with antimicrobials was determined, and the results were expressed as the lowest antimicrobial concentration that killed 99.90% of biofilm bacteria. Bacteria recovered from tests containing rifampin were tested for rifampin susceptibility.

In vitro bactericidal activity was observed for daptomycin against methicillin-resistant coagulase negative staphylococcal biofilms in 27 of 30 isolates with ≦32 μg/mL daptomycin. The emergence of rifampin resistance was detected in 5 of 27 isolates after exposure to rifampin and in 6 of 27 isolates after exposure to daptomycin plus 0.5 ug/nL of rifampin; daptomycin did not prevent emergence of rifampin resistance in MRCNS biofilms.

TABLE 3

Cidal activity of daptomycin and rifampin against susceptible *S. epidermidis* isolates in vitro.

| | Antimicrobial Concentration | | | | | | |
|---|---|---|---|---|---|---|---|
| | ≥64 | 32 | 16 | 8 | 4 | 2 | 1 |
| Daptomycin | | | | | | | |
| # of isolates | 10 | 2 | 1 | 5 | 4 | 5 | 0 |
| Mean $\log_{10}$ reduction | 2.0 | 3.6 | 3.5 | 3.8 | 3.2 | 3.3 | — |
| Range | 0.1-3.9 | 3.5-3.7 | — | 3.1-4.5 | 3.0-3.3 | 3.1-3.6 | — |
| Rifampin | | | | | | | |
| # of isolates | 21 (7) | 0 | 2 (1) | 2 | 1 | 0 | 1 (1) |
| Mean $\log_{10}$ reduction | 1.4 | — | 3.0 | 3.4 | 3.2 | — | 3.5 |
| Range | 0.8-3.0 | — | 3.0-3.0 | 3.6-3.2 | — | — | — |
| Daptomycin + Rifampin (0.5 ug/mL) | | | | | | | |
| # of isolates | 14 (5) | 2 (1) | 1 | 1 | 0 | 4 (1) | 5 (1) |
| Mean $\log_{10}$ reduction | 2.0 | 3.3 | 3.3 | 3.5 | — | 3.3 | 3.6 |
| Range | 0.2-3.4 | 3.0-3.6 | — | — | — | 3.1-3.5 | 3.1-4.1 |

(N) = number of rifampin susceptible isolates that became rifampin resistant during test

CONCLUSIONS

In vitro, daptomycin was cidal against stationary phase *S. epidermidis*, while vancomycin was not cidal.

In the rat Central Venous Catheter (CVC) biofilm model developed with *S. epidermidis* provided stable infections established in jugular catheters extending into the right atrium in rats. Biofilms (25 μm thickness) in catheters were observed by histopathology. A heavy infection ($10^5$) CFU/ml by blood draw through infected catheter was seen, while a lower infection density was observed in blood and organs (but was higher closest to catheter tip, e.g. vena cava, heart, lungs). Blood draws through infected CVC correlated with the infection level.

Daptomycin at 5 mg/ml (clinical infusion solution concentration) instilled in the catheter had therapeutic effect. At a shorter (30 min) exposure (5 mg/mL, QD×4) reduced biofilm to non-detectable level, but a resurgence of infection was common. A longer lock treatment (18 hours) exposure (5 mg/mL, QD×4) reduced biofilm to a non-detectable level and largely prevented resurgence of infection. Daptomycin instilled in lactated Ringer's (with calcium) exhibited a markedly superior efficacy compared to daptomycin instilled in saline.

While Vancomycin was equally effective (to daptomycin in Ringer's) in this model, against stationary phase *S. epidermidis* in vitro, daptomycin was cidal in lactated Ringer's, whereas vancomycin was not cidal. Finally, against methicillin resistant coagulate resistant staphylococci biofilms in vitro, daptomycin was cidal at lower concentrations than was rifampin.

The invention claimed is:

1. A method for treating a biofilm, comprising providing a solution of daptomycin in a lactated Ringer's solution to a biofilm.

2. The method of claim 1, wherein the biofilm is treated with the solution at least 30 minutes.

3. The method of claim 1, further comprising applying the solution to the biofilm until the biofilm is reduced.

4. The method of claim 3, wherein the biofilm is reduced and does not reoccur.

5. The method of claim 1, wherein the solution is applied to the biofilm for about 30 minutes.

6. The method of claim 1, wherein the solution is administered twice per day.

7. The method of claim 1, wherein the solution is administered at least four times per day.

8. The method of claim 1, wherein the concentration of daptomycin in the solution is at least 1 mg/mL.

9. The method of claim 1, wherein the concentration of daptomycin in the solution is at least 5 mg/mL.

10. A method of treating or preventing a biofilm, the method comprising exposing a surface of a device to a solution comprising daptomycin and calcium.

11. The method of claim 10, where the surface forms a portion of a catheter.

12. The method of claim 10, where the surface is an inner luminal surface of a catheter, and the surface is exposed to the solution by catheter lock therapy.

13. The method of claim 10, where the solution comprises about 5 mg/mL daptomycin and a physiological concentration of calcium.

14. The method of claim 12, where the catheter lock therapy comprises exposing a surface of the catheter to the solution for about 18 hours.

15. The method of claim 10, where the solution comprises daptomycin and lactated Ringer's solution.

16. The method of claim 11, further comprising performing a heparin flush of the catheter.

17. The method of claim 11, where the surface is exposed to the solution for at least about 30 minutes and the solution comprises about 5 mg/mL of daptomycin.

18. The method of claim 11, where the catheter is a central venous catheter.

19. The method of claim 10, where the method is a method of treating a biofilm in a catheter, the surface is an inner luminal surface of the catheter, and the solution comprises about 5 mg/mL daptomycin in lactated Ringer's solution.

20. A kit for the treatment of biofilm in a catheter comprising lactated Ringer's solution having daptomycin in an amount sufficient to treat the biofilm.

* * * * *